US006802318B1

(12) United States Patent  
Parker

(10) Patent No.: US 6,802,318 B1
(45) Date of Patent: Oct. 12, 2004

(54) TOE GUARD

(76) Inventor: Laura Ann Parker, HC 62 Box 106B, Great Cacapon, WV (US) 25422

(*) Notice: Subject to any disclaimer, the term of this patent is extended or adjusted under 35 U.S.C. 154(b) by 0 days.

(21) Appl. No.: 10/420,720

(22) Filed: Apr. 23, 2003

(51) Int. Cl.[7] .................................................. A61F 5/37
(52) U.S. Cl. ............................ 128/882; 602/23; 602/30
(58) Field of Search .............................. 128/882, 889, 128/890; 602/23, 30; 36/72 R, 77 R, 110

(56) References Cited

U.S. PATENT DOCUMENTS

| 1,375,690 A | | 4/1921 | George |
| 2,552,700 A | * | 5/1951 | Watts |
| 2,723,469 A | * | 11/1955 | Shusterman |
| 3,487,830 A | | 1/1970 | Pruett |
| 3,643,659 A | | 2/1972 | Sotrer |
| 4,177,583 A | * | 12/1979 | Chapman ..................... 36/77 R |
| 4,495,715 A | | 1/1985 | Fredrickson et al. |
| 4,566,208 A | | 1/1986 | Shaffner |
| 4,780,970 A | * | 11/1988 | McArthur ..................... 36/72 R |
| 5,074,060 A | * | 12/1991 | Brncick ....................... 36/77 R |
| 5,462,069 A | | 10/1995 | Cohen |
| 5,878,511 A | * | 3/1999 | Krajcir ....................... 36/77 R |
| 5,980,475 A | | 11/1999 | Gibbons |
| 2003/0213149 A1 | * | 11/2003 | Woods ........................ 36/110 |

* cited by examiner

Primary Examiner—Michael A. Brown
(74) Attorney, Agent, or Firm—Lawrence R. Franklin

(57) ABSTRACT

A toe guard is made of a flexible sheet of plastic, is U-shaped in longitudinal cross-section, is open in the back and both sides, and is contoured on its upper and lower surfaces to fit the top and bottom of a foot comfortably. The front of the toe guard is solid and is spaced from the toes when attached to the foot. The toe guard is attached by means of a wide strip of adhesive tape wrapped around the tongue and base of the guard in the vicinity of the instep and ball of the foot. The tape prevents the toe guard from slipping longitudinally on the foot. The toe guard protects the toes from a frontal impact and from blows from the top, bottom, and sides of the toe guard. The toe guard is initially wider than the foot for which it is designed and can be trimmed to fit the intended user's foot. Being flexible, it spreads to fit on the ball and instep, generally conforms to the shape of the foot, and bends with the foot when walking.

20 Claims, 4 Drawing Sheets

TOE GUARD

BACKGROUND OF THE INVENTION

1. Field of the Invention

This invention relates to a guard for the toes of a human foot. When a toe is injured, or when some or all of the toes have undergone surgery, the toes must be protected against impacts, not only such as occurs when the toes are stubbed, but from contact with all objects. At the same time, the toes should be unconfined so that healing air may freely circulate through and around them. It is also desirable that they be unrestricted to permit mild exercise by small, controlled movements without striking their protective covering. The disclosed and claimed invention satisfies the desiderata.

2. Description of Related Art

When an arm or leg, hand or foot, or finger or toe becomes injured, it is customary to bandage it to protect it against further damage. For arms legs, hands, and feet this usually takes the form of a cast, but casts for fingers and toes are usually contra-indicated. Instead, a guard is attached to the hand or foot with the guard surrounding the injured finger or toe.

Representative of prior art guards for fingers and toes are the U.S. patents to George (U.S. Pat. No. 1,375,690), Pruett (U.S. Pat. No. 3,487,830), Storer (U.S. Pat. No. 3,643,659), Fredrickson et al. (U.S. Pat. No. 4,495,715), Shaffner (U.S. Pat. No. 4,566,208), Cohen (U.S. Pat. No. 5,462,069), and Gibbons (U.S. Pat. No. 5,980,475), all of record.

George discloses a finger guard made of rigid sheet metal, preferably aluminum, comprising a U-shaped body which entirely covers the top and bottom of a finger with the sides of the two arms being curved to grip and substantially cover both sides of the finger. When the guard is secured to a bandaged finger by a strip of adhesive tape, the bight of the "U" is spaced from the tip of the finger. The guard of George differs considerably from the disclosed invention. First, George's finger guard is designed to fit a single finger in order to protect it while permitting free use of the rest of the hand; the disclosed invention is secured to the foot in order to protect from one to all of the toes. Second, the finger guard binds the top, bottom, and both sides of the finger, applying pressure to all but the tip of the finger; the toe guard contacts only the instep and ball of the foot, leaving the injured toes free from external contacts. Third, George's guard is attached to the base of the finger, so the vibrations from an imposed blow to the guard are transmitted to the finger bone and are therethrough returned to the injured portion of the finger, the very digit it is supposed to protect; the inventor's guard is anchored remote from the injured toe or toes to a larger, more absorbent part of the foot, so impacts are dampened before they can return to the toes. Fourth, George's finger guard is made of a rigid sheet of metallic material, which grips the finger like a brace or splint, holding the finger rigidly against movement; the disclosed toe guard is made of a plastic sheet which is flexible in order to bend to facilitate comfortable walking while rigidly opposing potentially damaging blows.

Pruett discloses a toe-covering sock which is attached to a cast by elastic straps. The sock is also made from an elastic material. The sock and straps combine to pull the sock against the toes which can apply painful pressure to sore toes. It covers them but does not protect them from injury. A thick sole is attached to the sock for walking, but it is not disclosed as being sufficient to perform a protective function. The instant toe guard is spaced from the toes, allowing them freedom from contact with surrounding structure while simultaneously shielding them from outside objects striking the toes.

Storer discloses a toe guard for keeping bedding away from the feet and toes when sleeping; it is not intended to prevent injury to the toes during normal activities while awake. Storer's guard band comprises a somewhat resilient, narrow, elongated element "shaped as an open loop to fit around the planform outline of the foot." The disclosure affirms that the band has "sufficient stiffness to retain its form while supporting bending," but it is not clear whether or not the loop will collapse into the toes under the force of a frontal impact. A heel cup is strapped to the foot by an instep strap and releaseably, adjustably supports the guard band, raising the question of whether the band could sustain a force applied to the toe loop without disengaging from the heel cup. The toe guard of Storer also exposes the top and sole of the foot, leaving the toes unprotected from objects on the floor that they may step on and from objects which may fall on them from above. The instant invention protects the toes from below, above, and from most intrusions from the sides.

Fredrickson et al. disclose a soft toe guard which is designed for protecting the toes during martial arts kicking. As such, the toe guard's protective cup has inner surfaces contoured to fit the hills and valleys of the foot from instep to arch to bind them together for increased rigidity, the same reason that a boxer's hands are taped. Straps hold the toe guard solidly against the toes and the foot. It is not intended to shield the toes from outside forces, merely to bind them together into a more compact, more solid, unified whole.

Shaffner discloses a toe guard comprising rails attached to opposite sides of a cast or surgical shoe with rails connected across the front of the toes. Unlike the disclosed invention, Shaffner's rails do not protect the top nor bottom of the foot, and an object can easily penetrate between the front rails to further injure the toes. Further, Shaffner's rails must be supported by being attached to a cast on the foot. The inventive toe guard disclosed herein is attached directly to the foot.

Cohen discloses a rigid toe guard having a foot support, an enclosed toe cap, and a top tongue. The toe guard is either strapped to a foot, in which case it pulls the toe cap against the toes, or releasably connected to a surgical shoe, in which case the shoe prevents the toe guard from sliding relative to the foot. It is not flexible, it rubs against the toes, and it requires a shoe to maintain it from sliding on the foot.

Gibbons discloses a rigid toe guard comprising a solid cap which just covers the toes. The toe guard either fits within a surgical shoe or is held on by elastic straps which pulls the guard into contact with the toes. Holes provide ventilation. It is not flexible, rubs against the toes, and either requires a shoe to maintain it from sliding on the foot or a strap which pulls it against the toes.

OBJECTS AND SUMMARY OF THE INVENTION

The present invention overcomes the difficulties described above by providing a unitary toe guard which completely covers the bottom, front, and top of the toes while being maintained spaced therefrom. It is a flexible sheet of plastic which bends with the foot while walking but rigidly shields the toes from outside contacts.

It is an object of the invention to provide a toe guard which is simple in construction, inexpensive to manufacture, and effective in practice.

It is a further object of the invention to provide a toe guard which comprises an integral structure made from a flexible sheet of plastic material.

It is a further object of the invention to provide a toe guard which covers all of the toes and protects them from injuries due to stubbing the toes, from stepping on objects on the ground, and from objects falling onto the toes.

It is a further object of the invention to provide a toe guard which can be trimmed to fit the foot.

BRIEF DESCRIPTION OF THE DRAWINGS

The foregoing and other objects, aspects, uses, and advantages of the present invention will be more fully appreciated as the same becomes better understood from the following detailed description of the present invention when viewed in conjunction with the accompanying drawings, in which.

DETAILED DESCRIPTION OF THE PREFERRED EMBODIMENT

Figure 1:
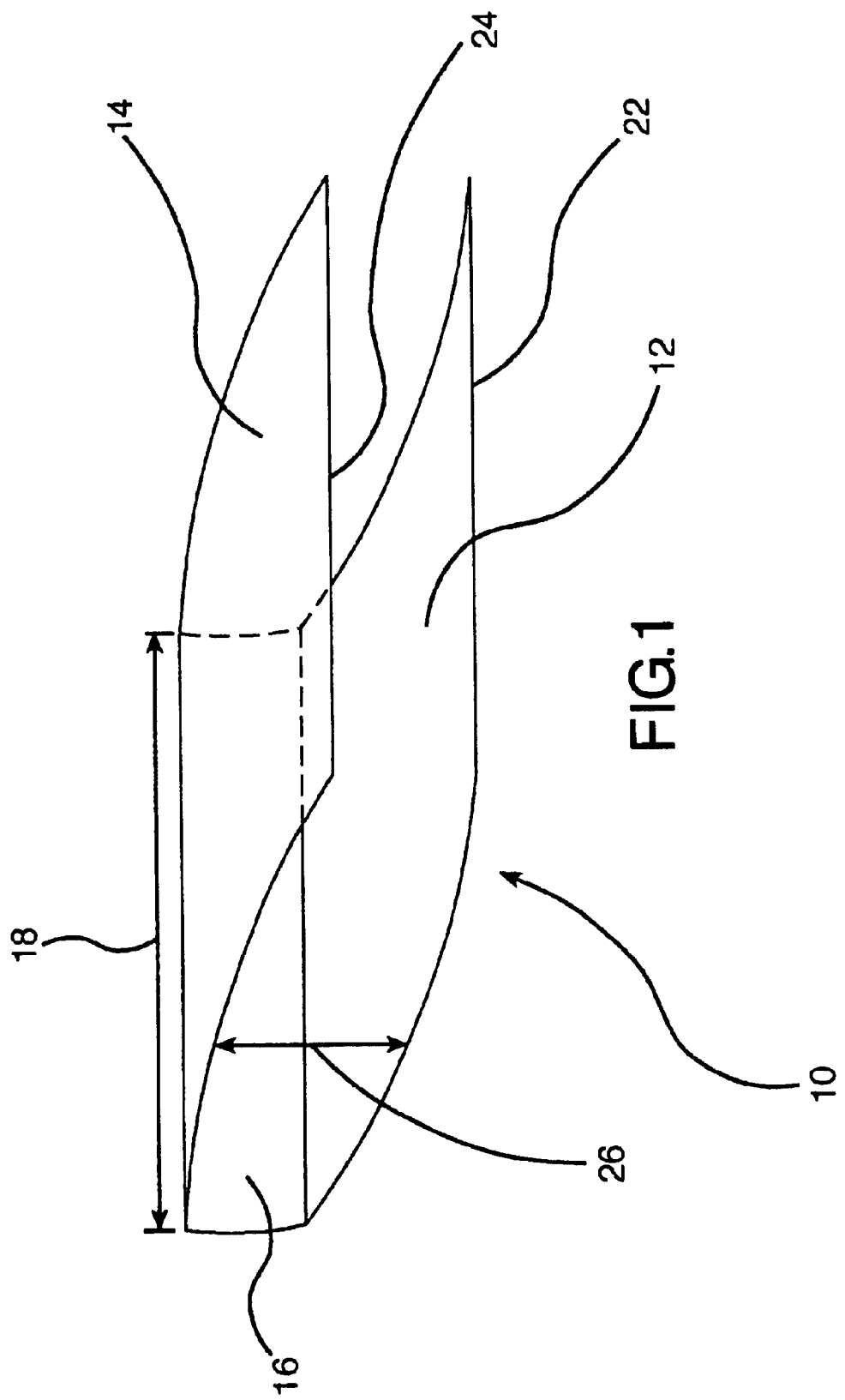
FIG. 1 is a perspective view which illustrates one preferred embodiment of the present invention.

Referring to FIG. 1, a toe guard 10 is shown in perspective. Toe guard 10 is U-shaped as seen in side view (FIG. 2) and comprises a sole 12, a tongue 14, and a bight 16 integrally connecting sole 12 to tongue 14.

Toe guard 10 is preferably made from a high density polyethylene (HDPE) with a thickness between 0.025" and 0.028". This combination has been found to be lightweight, flexible enough to be comfortable, and rigid enough to protect the toes from external impacts. The material HDPE has another advantageous property: it can easily be trimmed by the wearer with an ordinary pair of scissors to fit the foot. Toe guard 10 can thereby be customized to the individual. Other materials and thicknesses which provide the necessary flexibility and rigidity are within the purview of the disclosure and claims, however.

It is contemplated that toe guard 10 be produced in different sizes, e.g., S, M, L, XL, XXL, etc., to fit different sized feet. Each size is intended for a selected range of foot sizes.

For simplicity of manufacture, it is preferred that the length of sole and tongue (from bight 16 to their free ends) be the same and that the widths of the sole, tongue, and bight (FIG. 1, width 18) be the same. The major surfaces of sole, tongue, and bight will be substantially rectangular, therefore, as seen in FIG. 1. The invention is not limited thereto, however. The length of the sole may be manufactured longer than that of the tongue in order to better approximate the difference in distance from the toes to the instep and from the toes to the arch. Their instantaneous width as progressing from their bight to their free ends may also change, either smoothly, deliberately, or due to manufacturing tolerances. The exact initial configurations are not critical to the concepts and principles of the invention.

The important length considerations, relative to the foot for which it is intended, of course, are that the tongue be longer than the distance from the tip of the toes to the ankle end of the instep and the sole be longer than from the tip of the toes to the heel end of the arch. Extra lengths can be trimmed to fit the foot of the user. The important width consideration is that the minimum width be wider than the maximum width of the foot for which it is intended. Trimming of the sides will be discussed in more detail shortly.

Figure 2:
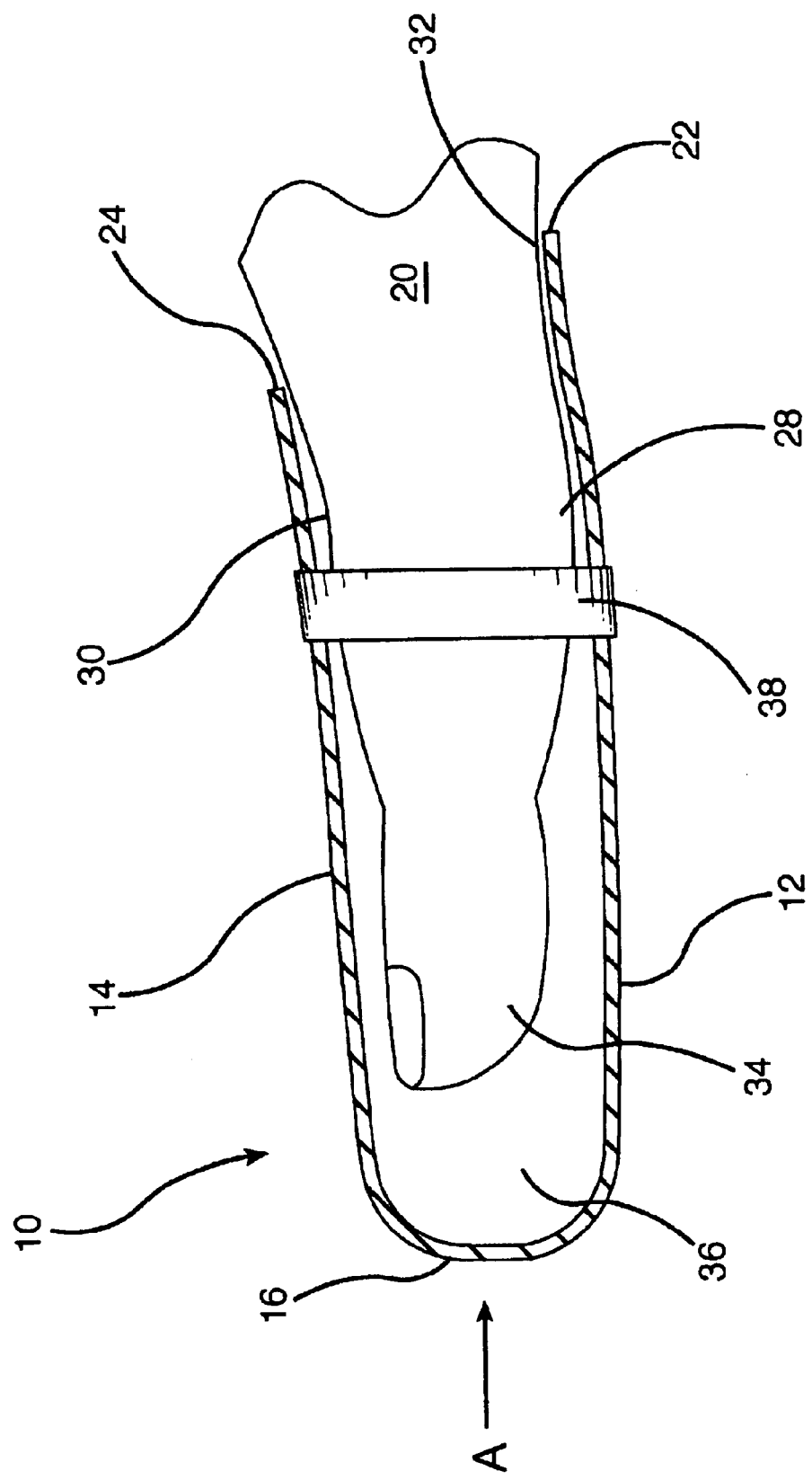
FIG. 2 is a cross-sectional side view of the toe guard of FIG. 1 as seen along lines II—II of FIG. 3.
Figure 3:
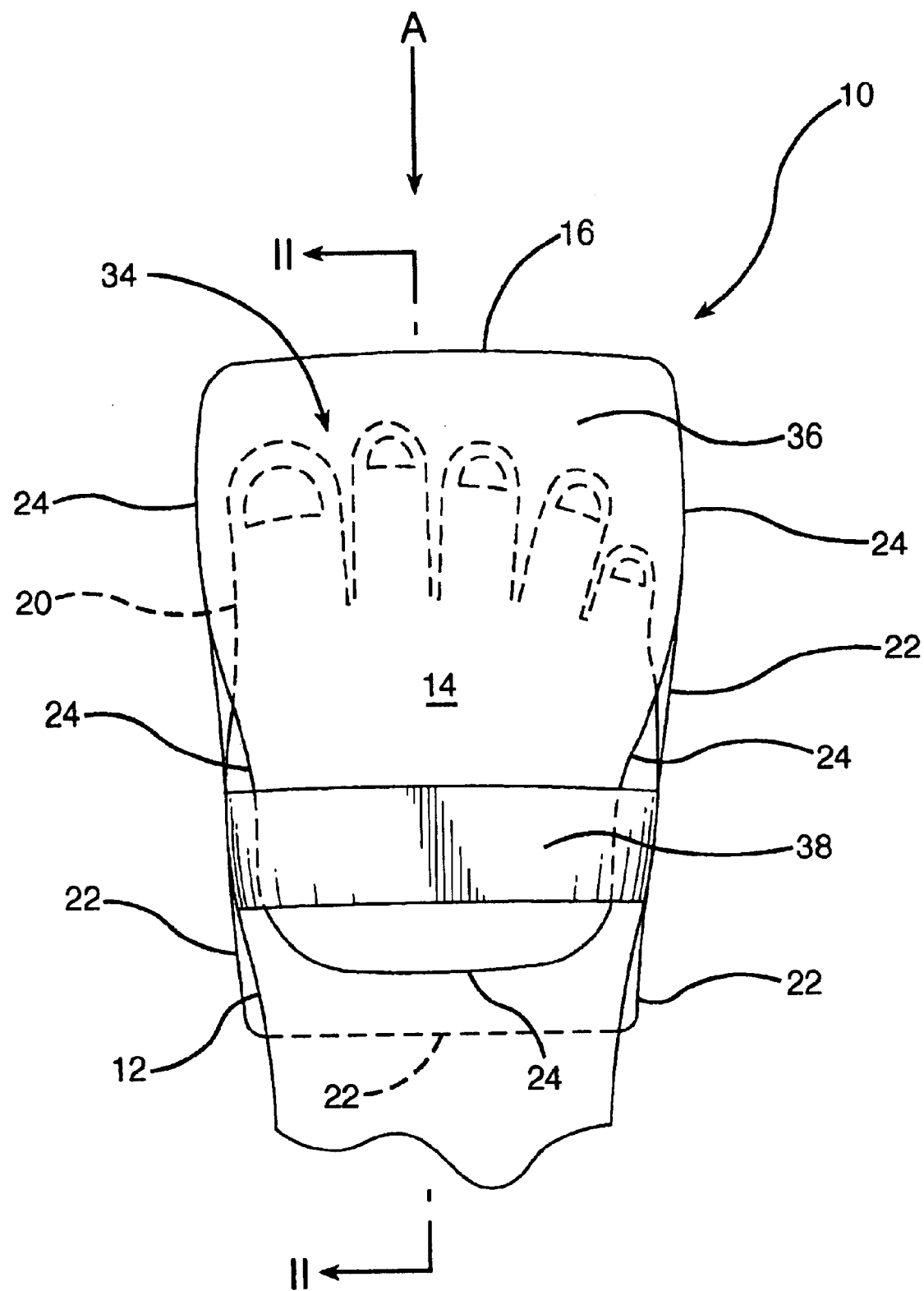
FIG. 3 is a top view of the toe guard of FIG. 1 as attached to a human foot.

As can be seen in FIG. 2 where a foot 20 is shown in side perspective and toe guard 10 is shown in cross-section along lines II—II of FIG. 3, guard 10 fits over the end of the human foot 20 with sole 12 sliding beneath the ball 28 of foot 20 and the tongue 14 resting on the instep 30 of foot 20. Because HDPE is slightly flexible across the major surface areas, sole 12 and tongue 14 will bend vertically at their junctures with bight 16 (FIG. 2) and along lines transverse their lengths to expand enough to encompass ball 28 and instep 30 of foot 20. Because of its rectangular shape and limited height, bight 16 will resist any attempt to twist sole 12 and tongue 14 about axes orthogonal to bight 16. As a consequence, toe guard 10 conforms quite well to the shape of foot 20 and easily maintains its fit during normal use.

Sole 12 is trimmed by the wearer so that the transverse portion of the peripheral edge 22 of sole 12 ends just beyond ball 28 and about midway through arch 32. The transverse portion of the peripheral edge 24 of tongue 14 is trimmed just beyond instep 30. It has been determined that trimming in this manner produces a very comfortable toe guard. It should be noted that toes 34 do not come into contact with toe guard 10. A void 36 surrounds toes 34 and allows them a limited amount of flexure, permitting them to be mildly exercised. Void 36 coupled with the open sides allows soothing air to flow freely around toes 34.

Turning to FIG. 3, a top view of toe guard 10 as fit on foot 20 is shown. The peripheral edges 22 and 24 of sole 12 and tongue 14, respectively, are trimmed as shown so that their side edges extend laterally beyond the side edges of foot 20, thereby protecting the sides of foot 20 from being struck by large objects. Only relatively pointed objects having a height less than the distance 26 (FIG. 1) between sole 12 and tongue 14 can intrude between them. It is rare that one strikes either side of the foot against any object, since the feet are rarely swung sideways, so leaving the sides of toe guard 10 open does not expose the foot to a sizable amount of danger.

The most common danger for injured toes is from a frontal impact, represented by the force vector arrow A in FIGS. 2 and 3, such as is produced by stubbing them while walking. Guard 10 is especially effective in protecting toes 34 against such an assault.

A sizeable gap 36 exists between the ends of toes 34 and bight 16 (FIGS. 2–3). When subjected to a force A, the impact attempts to drive guard 10 longitudinally of foot 20, in the direction of arrow A toward toes 34 and up foot 20 toward the ankles, bringing bight 16 into painful contact with sore toes 34. To prevent this type of movement, guard 10 is secured on foot 20 by a strip of adhesive tape 38 wrapped around sole 12 and tongue 14 adjacent their free ends. Tape 38 binds sole 12 and tongue 14 to foot 20 by clamping down on foot 20 within the plane defined by the loop of tape. That is, the fastening force is generally orthogonal to the length of said foot, so that no binding force components are present which would tend to pull toe guard 10 along foot 20 into contact with toes 34, as is experienced with certain prior art toe guards mentioned previously. Thus, toe guard 10 is attached to foot 20 by a mechanism which is free from longitudinal tensions which could cause movements of guard 10 longitudinally relative to foot 20. In light of the operational principles of this mechanism, other connectors or fasteners are contemplated as being equivalent to tape 38. For instance, either an endless, elastic band or a length of elastic material with mating Velcro™ strips on the ends will also grip sole 12 and tongue 14 vertically through foot 20 tightly enough to resist longitudinal relative movement of guard 10 on foot 20. The elastic bands or strips can be provided separately or as attached either permanently or releaseably to toe guard 10. All such embodiments are considered within the scope of the claimed invention. Tape is preferred, however, for its comfort and for its ease of application and replacement on the affected foot.

The periphery of tongue 14 is preferably trimmed as shown in FIG. 3 for comfort and to expose enough surface area of foot 20 to permit adequate contact of tape 38 therewith to secure guard 10 thereto. The periphery of sole 12 is also preferably trimmed to fit the width of the ball 28 of foot 20 for comfort and so that no sharp edges extend beyond the width of foot 20 which might tend to cut into tape 38 and thereby weaken it.

When the toes are accidentally stubbed, force A is resisted by the combination of bight 16, sole 12, and tongue 14. The preferred slight curvature of bight 16 shown in FIG. 2 directs the force components of force A into the plane of both sole 12 and tongue 14. Even though the material of toe guard 10 is transversely flexible enough to allow sole 12 and tongue 14 to bend sufficiently to fit ball 28 and instep 30 and to follow their movements when the patient is walking, sole 12 and tongue 14 cannot be bent by forces directed within their planes. Thus, stubbing force A cannot collapse sole 12 and tongue 14 enough to allow bight 16 to come into contact with toes 34. Also, since tape 38 prevents the movement of guard 10 relative to foot 20, guard 10 is prevented from being moved en masse into contact with toes 34. Finally, bight 16 cannot be bowed inwardly against toes 34 by force A, because the height 26 of bight 16 is too small to allow it to bend inwardly enough to cross void 36. Thus, toes 34 are completely protected by guard 10 from frontal impacts.

Toes 34 are also shielded from blows from above and below foot 20.

Nothing can completely protect injured toes from an object dropped from above onto the toes. But, guard 10 minimizes the effects. As seen most clearly in FIG. 2, tongue 14 is supported at its opposite ends by bight 16 and instep 30; tongue 14 is maintained spaced above toes 34 by the combination. A blow anywhere on the top of tongue 14 is diffused throughout, which spreads the effects thereof. Tongue 14 will bow downwardly, but since HDPE stretches very little, most of the forces are absorbed by instep 30 and bight 16.

Stepping on a pebble or other sharp object can be very painful to any foot but more so to sore toes. Having sole 12 between the toes and the ground protects the toes from direct contact in the manner of any sole.

Figure 4A:
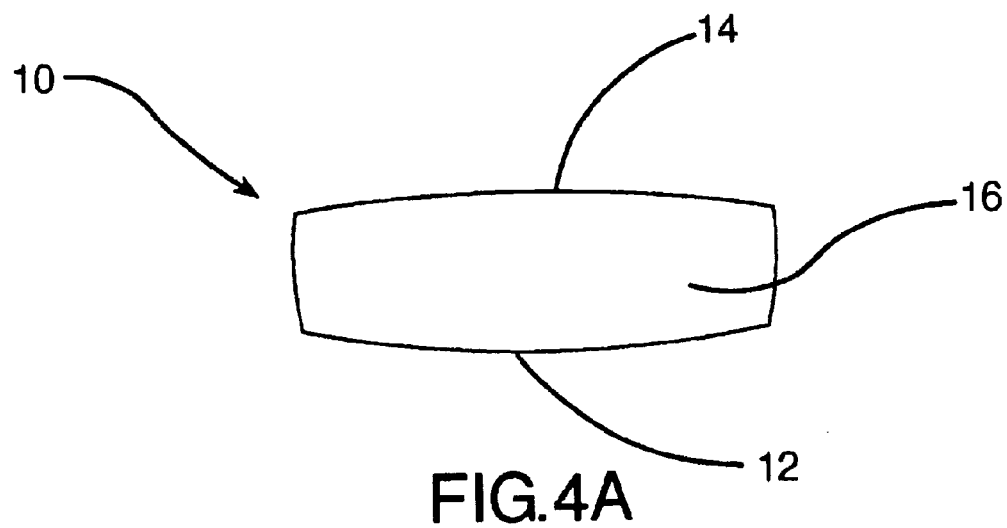
FIGS. 4A–4C are front views of the toe guard of FIG. 1 showing alternative configurations for the tongue and sole.
Figure 4B:
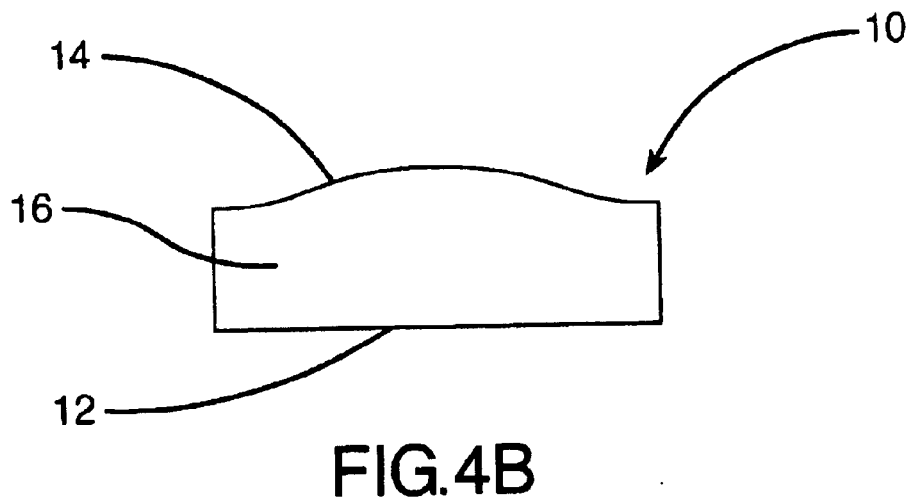
Figure 4C:
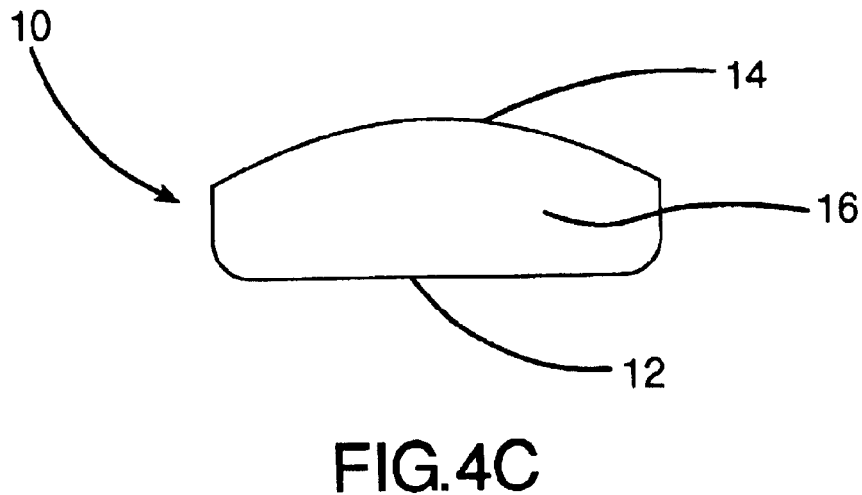

Turning to FIGS. 4A–4C, front views of three embodiments of preferred contours of sole 12, tongue 14, and bight 16 are shown. The material HDPE with a thickness as stated, i.e., 0.025" to 0.028", is flexible enough to conform to the sole and instep of foot 20, when bound thereto by tape 38. Thus, guard 10 can effectively be manufactured with a substantially flat sole 12 and a substantially flat tongue 14 as indicated in FIG. 1. This does not preclude, however, the desirability of molding sole 12 and tongue 14 to have a cross-sectional configuration which substantially matches the common cross-sectional shape of the sole and instep of human feet. FIG. 4A shows sole 12 and tongue 14 slightly rounded which facilitates the foot-conforming process.

Tongue 14 is deliberately arched in FIG. 4B to more closely fit the contours of instep 30 while sole 12 is maintained substantially flat. And, unlike FIG. 4B where the four corners of bight 16 are substantially square, the toe guard 10 of FIG. 4C rounds them, especially the lower ones, thus contouring guard 10 to more closely, and thereby more comfortably, fit the foot.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention as defined in the appended claims.

Further, the purpose of the foregoing Abstract is to enable the U.S. Patent and Trademark Office, and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of the application, which is measured solely by the claims, nor is intended to be limiting as to the scope of the invention in any way.

It can be seen from the above that an invention has been disclosed which fulfills all the objects of the invention. It is to be understood, however, that the disclosure is by way of illustration only and that the scope of the invention is to be limited solely by the following claims:

I claim as my invention:

1. A toe guard to protect the toes of a human foot from externally imposed forces, said toe guard comprising:
   a sole, a tongue, and a bight;
   said sole, tongue, and bight being integrally connected together, made of flexible plastic material, and configured so that when said toe guard is placed on the human foot, said sole extends beneath the ball of said foot, said tongue extends over the instep of said foot, and said bight is spaced from the ends of said toes such that a void is formed between said toes and said toe guard; and
   a connector for fastening said toe guard to said foot, said connector encircling said foot between the ankle and said toes of said foot.

2. The toe guard of claim 1 wherein said plastic material of which said toe guard is made comprises a high density polyethylene.

3. The toe guard of claim 2 wherein said high density polyethylene has a thickness substantially between 0.025" and 0.028".

4. The toe guard of claim 2 wherein said high density polyethylene is slightly flexible across the major surface areas of said sole and said tongue such that said toe guard conforms generally to the shape of said foot.

5. The toe guard of claim 1 wherein said toe guard is U-shaped when viewed from the side and is open on the sides.

6. The toe guard of claim 5 wherein said tongue is cross-sectionally configured to more closely conform to the cross-sectional shape of a normal human foot.

7. The toe guard of claim 5 wherein said connector comprises a strip of adhesive tape extending around said toe guard along a path comprising over the top of said tongue, under the bottom of said sole, and across both of said open sides.

8. The toe guard of claim 5 wherein said connector comprises an endless elastic band extending around said toe guard along a path comprising transverse said tongue, transverse said sole, and across both of said open sides.

9. The toe guard of claim 8 wherein said elastic band is attached to said toe guard.

10. The toe guard of claim 5 wherein said connector comprises a length of elastic material with mating Velcro™ strips on the ends-extending around said toe guard along a path comprising transverse said tongue, transverse said sole, and across both of said open sides.

11. The toe guard of claim 10 wherein said length of elastic is attached to said toe guard.

12. A toe guard to protect the toes of a human foot from externally imposed forces, said toe guard being generally dimensioned to fit a predetermined range of sizes of a human foot, said toe guard comprising:
   a sheet of flexible plastic material defining a sole, a tongue, and a bight, said bight being located between said sole and said tongue and being integrally connected therewith, and said sole and said tongue extending away from said bight such that said toe guard is generally U-shaped when viewed from the side and is open on the sides;
   the minimum width of said sole, tongue, and bight being wider than the maximum width of the selected human foot for which said toe guard is generally dimensioned;
   the length of said sole extending away from said bight being such as to extend beneath the ball of said selected foot and beneath at least a portion of the arch of said selected foot;
   the length of said tongue extending away from said bight being such as to extend over the instep of said selected foot; and
   the height of said bight being such that when said toe guard is placed on said selected human foot, a void is formed between said toes and said toe guard; and
   a connector for fastening said toe guard to said selected foot against longitudinal sliding movement along said selected foot.

13. The toe guard of claim 12 wherein said plastic material comprises a high density polyethylene.

14. The toe guard of claim 13 wherein said high density polyethylene has a thickness substantially between 0.025" and 0.028".

15. The toe guard of claim 13 wherein said toe guard is capable of being trimmed to fit said selected human foot.

16. The toe guard of claim 13 wherein said high density polyethylene is flexible across the major surface areas of said sole and said tongue such that said toe guard conforms to the shape of said selected foot while said bight is rigid enough to withstand impacts without collapsing into contact with said toes.

17. The toe guard of claim 16 wherein said tongue and said sole are molded to generally conform to the general shape of said selected human foot.

18. A toe guard to protect the toes of a human foot from externally imposed forces, said toe guard comprising:
   a sole, a tongue, and a bight;
   said sole, tongue, and bight being integrally connected together, made of flexible plastic material, and configured so that when said toe guard is placed on the human foot, said sole extends beneath the ball of said foot, said tongue bends to fit over the instep of said foot, said bight is spaced from the ends of said toes, and a void is formed between said toes and said toe guard; and
   a connector for fastening said toe guard to said foot, said connector comprising a strip extending around said ball and said instep of said foot with the binding forces being generally orthogonal to the length of said foot such that no binding force components tend to pull said toe guard into contact with said toes.

19. The toe guard of claim 18 wherein said connector comprises a strip of adhesive tape extending around said toe guard along a path comprising over the top of said tongue, under the bottom of said sole, and across both of said open sides.

20. The toe guard of claim 18 wherein said connector comprises an endless elastic band extending around said toe guard along a path comprising over the top of said tongue, under the bottom of said sole, and across both of said open sides.

* * * * *